United States Patent
Thalgott

[19]

[11] Patent Number: 5,865,845
[45] Date of Patent: Feb. 2, 1999

[54] PROSTHETIC INTERVERTEBRAL DISC

[76] Inventor: John S. Thalgott, 600 S. Rancho, Ste 107, Las Vegas, Nev. 89106

[21] Appl. No.: 609,593

[22] Filed: Mar. 5, 1996

[51] Int. Cl.$^6$ ........................................................ A61F 2/44
[52] U.S. Cl. ............................................................ 623/17
[58] Field of Search ........................... 623/17, 16; 606/60, 606/61

[56] References Cited

U.S. PATENT DOCUMENTS

| | | |
|---|---|---|
| 4,349,921 | 9/1982 | Kuntz . |
| 4,479,491 | 10/1984 | Martin . |
| 4,655,777 | 4/1987 | Dunn et al. . |
| 4,714,469 | 12/1987 | Kenna . |
| 4,759,766 | 7/1988 | Beuttner-Janz et al. . |
| 4,863,476 | 9/1989 | Shepperd . |
| 4,863,477 | 9/1989 | Monson . |
| 4,874,389 | 10/1989 | Downey . |
| 4,904,261 | 2/1990 | Dove et al. . |
| 4,911,718 | 3/1990 | Lee et al. . |
| 4,917,704 | 4/1990 | Frey et al. . |
| 4,932,969 | 6/1990 | Frey et al. . |
| 4,936,848 | 6/1990 | Bagby . |
| 4,946,378 | 8/1990 | Hirayama et al. . |
| 4,955,908 | 9/1990 | Frey et al. . |
| 4,961,740 | 10/1990 | Ray et al. . |
| 4,997,432 | 3/1991 | Keller . |
| 5,002,576 | 3/1991 | Fuhrmann et al. . |
| 5,035,716 | 7/1991 | Downey . |
| 5,047,055 | 9/1991 | Bao et al. . |
| 5,055,104 | 10/1991 | Ray . |
| 5,071,437 | 12/1991 | Steffee . |
| 5,108,438 | 4/1992 | Stone . |
| 5,123,926 | 6/1992 | Pisharodi . |
| 5,171,281 | 12/1992 | Parsons et al. . |
| 5,192,326 | 3/1993 | Bao et al. . |
| 5,192,327 | 3/1993 | Brantigan . |
| 5,258,043 | 11/1993 | Stone . |
| 5,306,308 | 4/1994 | Gross et al. . |
| 5,306,309 | 4/1994 | Wagner et al. . |
| 5,314,477 | 5/1994 | Marnay . |
| 5,314,478 | 5/1994 | Oka et al. . |
| 5,320,644 | 6/1994 | Baumgartner . |
| 5,370,697 | 12/1994 | Baumgartner . |
| 5,401,269 | 3/1995 | Buttner-Janz . |
| 5,571,189 | 11/1996 | Kuslich ..................................... 623/17 |
| 5,571,190 | 11/1996 | Ulrich et al. .............................. 623/17 |
| 5,609,635 | 3/1997 | Michelson ................................. 623/17 |
| 5,645,596 | 7/1997 | Kim et al. ................................. 623/17 |

FOREIGN PATENT DOCUMENTS

| | | | |
|---|---|---|---|
| 0599419 | 1/1994 | European Pat. Off. .................. 623/17 |
| 4004400 | 3/1994 | WIPO ..................................... 623/17 |
| 4006213 | 11/1994 | WIPO ..................................... 623/17 |

*Primary Examiner*—Debra S. Brittingham
*Attorney, Agent, or Firm*—Cooper & Dunham LLP

[57] ABSTRACT

The invention provides a spinal disc implant comprising a ring shaped body including a first pair of opposed substantially parallel sides spaced apart by a second pair of opposed sides to define a central bore. A first one of the second pair of sides defines a substantially arcuate curve joining a first end of the first pair of sides. A second one of the second pair of opposed sides substantially linearly joins a second end of the first pair of sides. The upper and lower surfaces of the ring shaped body have a plurality of teeth extending therefrom for engaging adjacent vertebrae. The implant is made of a biocompatible metal such as titanium or an alloy thereof, and the first and second sides tapering from the second end to the first end. The interior space may have a porous hydroxyapatite block shaped to fill the interior space. The porous hydroxyapatite substance helps the prosthesis integrate into the vertebral structure by allowing one grow into the pores.

9 Claims, 1 Drawing Sheet

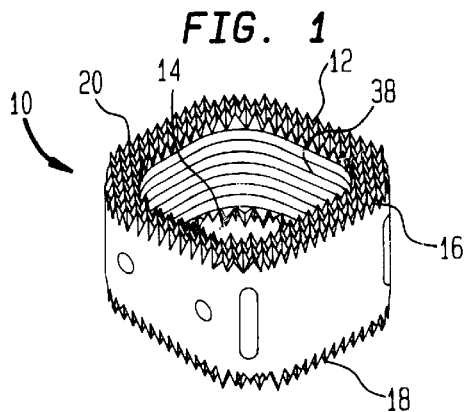
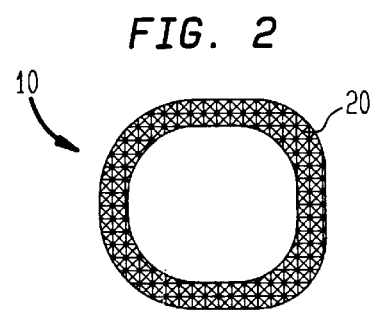
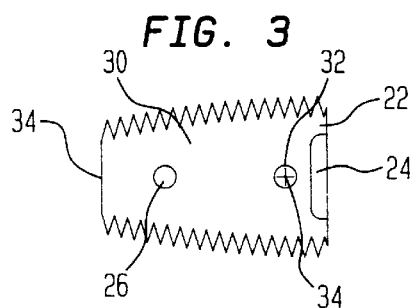
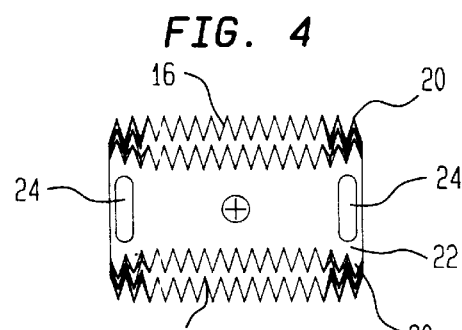
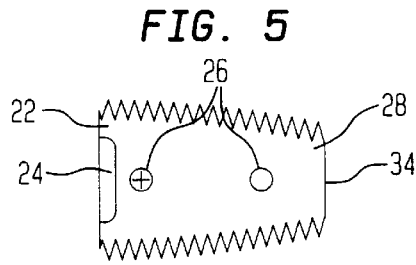
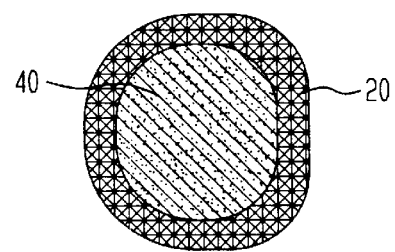
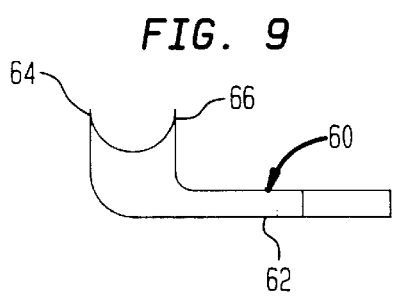
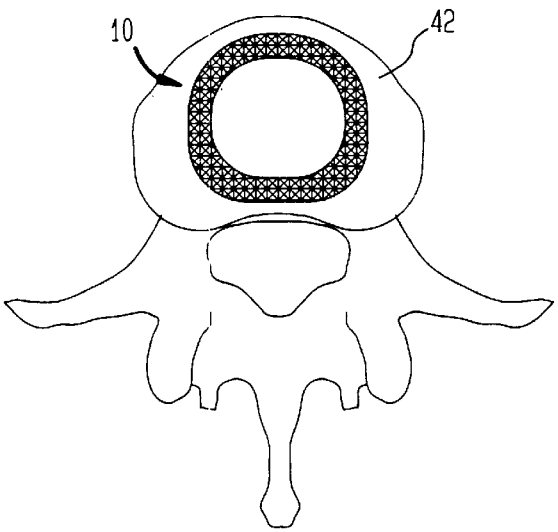

PROSTHETIC INTERVERTEBRAL DISC

FIELD OF THE INVENTION

This invention relates to artificial biocompatible vertebral synthetic devices and more particularly to prosthetic metal intervertebral discs, and methods and tools for implanting such prostheses.

BACKGROUND OF THE INVENTION

Many types of vertebral prostheses have been proposed and patented for implantation in the vertebral disc space after surgical removal of a diseases or damaged disc. Such devices fall into several broad categories. One category includes prostheses advocates the use of pliable synthetic materials in an attempt to mimic the compressibility of the natural human spinal disc. For example, U.S. Pat. No. 5,171,281 (Parsons) discusses a disc spacer which purports to possess mechanical properties akin to those of the normal disc by varying the hardness of the elastomeric material in its nucleus and annulus. U.S. Pat. No. 5,192,326 (Bao) illustrates a prosthetic disc formed from a multiplicity of hydrogel beads having a water content of at least 30%. A semi-permeable membrane covers the beads and is said to permit fluids to flow in and out of the prosthetic nucleus. U.S. Pat. No. 5,071,437 (Steffee) has another approach to a pliable implant. That approach involves upper and lower flat rigid plates sandwiching an elastomeric core made from a polyolefin rubber. U.S. Pat. No. 5,002,576 (Fuhrmann) also discusses a variant on the foregoing approach.

Another approach involves attempts to mimic the shape of a natural spinal disc. U.S. Pat. No. 4,714,469 (Kenna) discusses a spinal implant adapted to replace a disc between adjacent vertebrae using a predetermined thickness and profile to match the space between the vertebrae. The implant includes a porous coating on its surface. U.S. Pat. No. 4,759,766 (Buettner-Janz) illustrates a metallic disc endoprosthesis which has two symmetrical, concave end plates with an intermediate spacing piece. Similarly, U.S. Pat. No. 5,314,477 (Oka) discusses a disc prosthesis including two plates separated by a joint composed of a spherical cap and cylindrical base which attempts to ensure connection between the vertebrae.

Some prostheses emphasize mimicking the shape of the space formed by adjacent vertebral bodies. For example, according to the patentee of U.S. Pat. No. 5,320,644 (Baumgartner), he provides a disc prosthesis having a wedge shape having a wedge angle from the ventral to the dorsal side. The patent says the disc has parallel slits arranged at a right angle to its axis which partly overlap one another, forming leaf springs for transmission of forces from one attachment surface to another. U.S. Pat. No. 5,306,309 (Wagner) provides a spinal disc implant having a right rectangular body including two opposed side faces and two opposed transverse faces. According to the patentees, a convexly curved anterior face defines one end of the right rectangular body, and an outwardly curved face of about that of the anterior surface of a human vertebra.

Each of the foregoing prostheses, however, while addressing some problems, presents others. It is therefore a principal object of the invention to provide a disc prosthesis whose design takes into consideration the anatomy and particularly the geometry of the intervertebral space sought to be filled by the prosthetic device. It is an important and further object to provide a spinal disc prothesis which integrates well with the vertebral bone tissue of adjacent vertebral bodies between which the device is inserted.

SUMMARY OF THE INVENTION

The foregoing objects are achieved and the disadvantages of the prior art are overcome by providing a spinal disc implant comprising a first pair of opposed substantially parallel sides spaced apart by a second pair of opposed sides to define an interior space. A first one of the second pair of sides defines a substantially elliptical curve joining a first end of the first pair of sides. A second one of the second pair of opposed sides substantially linearly joins a second end of the first pair of sides. The upper and lower edges of the implant have a plurality of teeth extending therefrom for engaging adjacent vertebrae. The implant is made of a biocompatible metal such as titanium or an alloy thereof, and the first and second sides tapering from the second end to the first end.

Preferably, the interior space has a porous hydroxyapatite block shaped to fill the interior space. The porous hydroxyapatite substance helps the prosthesis integrate into the vertebral structure by allowing bone grow into the pores.

BRIEF DESCRIPTION OF THE DRAWINGS

Other features and advantages of the invention will be apparent from the following detailed description of the preferred embodiments taken in conjunction with the accompanying drawings in which:

FIG. 1 is a perspective view of the spinal disc implant of the present invention;

FIG. 2 is a top view of the spinal disc implant of FIG. 1;

FIG. 3 is a view of one side of implant of FIG. 1;

FIG. 4 is a front view of the spinal disc implant of FIG. 1;

FIG. 5 is a side view of the spinal disc implant of the side opposite from FIG. 3;

FIG. 6 is a rear view of the spinal disc implant of FIG. 1;

FIG. 7 is a top view of another preferred embodiment of the spinal disc implant of FIG. 1, wherein the open portion is filled with porous hydroxyapatite; and FIG. 8 is a plan view of a cervical vertebra with the spinal disc implant of FIG. 1 shown in phantom (dashed) lines positioned thereon.

FIG. 9 is plan view of an implantation tool for use in implanting the spinal disc implant of FIG. 1.

DETAILED DESCRIPTION OF THE PREFERRED EMBODIMENTS

FIG. 1 illustrates a spinal disc implant of the present invention generally indicated by the reference numeral 10. The implant 10 has a generally D-shaped body 12 including a central opening 14. The implant further 10 includes first and second faces 14, 16 having a plurality of teeth 20 or other gripping means included on each face.

Referring to FIG. 4, the front side of the implant 22 has at either edge thereof a pair of vertical oval shaped slots 24 used for gripping and positioning the implant 10 during surgery. The implant 10 additionally has one or more central circular notches 26 which a prong of a surgical tool (not shown) can engage to help position the implant 10. The first lateral side 28 of the implant 10 (illustrated in FIG. 5) includes two circular notches or dimples 26 to engage a pair of prongs (64, 66) for a surgical implantation tool 60, shown in FIG. 9. FIG. 3 illustrates or shows a second lateral side 30 which includes a notch 26 and a hole into which a set screw 34 is tightened so that it is flush with the surface of the second lateral side 30, as shown in FIG. 3. The rear side of the implant 35 includes a hole 36 similar to the one discussed in connection with the second lateral side 30. Once again, a set screw 34 is tightened into the hole 36 so that it is flush with the surface of the rear side 35. The interior surface 38 of the implant (see FIG. 1) has a series of circumferential scorings 40 to help hold by friction any material inserted in the central opening 14.

The teeth 20 (best shown in FIG. 2) are preferably steeply sloped four-sided pyramids arranged in straight rows across and down the first and second faces 16, 18 of the implant 10 as shown in FIG. 2. The pyramidal faces preferably form a 45° angle with the vertical. They can be formed by machining the implant 10.

An important aspect of the present invention is its geometric compatibility with its environment Referring to FIGS. 3 and 5, the implant 10 slopes from the front or anterior side 22 to the rear or posterior side 34. This shape enables the implant 10 to fit between adjacent vertebral bodies 42 (see FIG. 8) when the spine is in an upright position. The exact angle formed at the vertex defined by the first and second faces 16, 18 varies depending on which disc is being replaced. In the lumbar region of the spine, for example, the opposed faces adjacent vertebral bodies define an angle ranging from about 0 to about 20degrees. Similarly, since the vertebral body 42, which engages the first and second faces 16, 18 from above and below, has curvature, the implant 10 also has curvature to allow it to conform to the domed shape the vertebral body surface.

The implant 10 is preferably made from pure titanium or an alloy thereof, preferably anodized to increase its biocompatiblity by making it more inert. The implant 10 may be made from bar stock, or tubing or by molding; or from titanium powder using powder metallurgy technique. The dimensions of the implant 10 vary depending on where in the spine the implant will be inserted. The vertebral bodies in the lumbar area of spine, for example, are larger than the vertebral bodies in the thoracic area. Therefore, an implant intended for the thoracic region would be smaller than one for the lumbar region. Likewise, lower lumbar disc replacements would be larger than upper ones. By way of example, an implant sized for implantation between the third and fourth lumbar vertebrae may be 2.7 cm. long, 2.5 cm wide, about 2 cm high anteriorly, and sloping down to about 1.3 cm high posteriorly. A person of ordinary skill could adapt the basic dimensions of the implant to make them occupy for the space formerly occupied by the particular vertebral disc which needs replacement.

The shape and curvature of the first and second faces 16, 18 of the implant 10 provide several advantages. In the lumbar region of the spine, the discs and vertebral bodies 42 are held at an angle creating a lordosis or curvature of the lumbar spine. To have the implant 10 be parallel or coplanar would be physiologically and anatomically unacceptable. The natural discs in the lumbar spine are wider anteriorly than they are posteriorly. The disc replacement implant 10 of the present invention is therefore also wider anteriorly than it is posteriorly. This recreates the natural anatomic curvature of the spine.

Further, the implant 10 of the present invention takes into consideration the anatomy of the undersurface of the vertebral body or end plate of the vertebra on which the second face 18 of the implant 10 rests. The end plate is made of very compact bone circumferentially, but as the bone centralizes towards the middle, it becomes thinner. The thinner portion is dome shaped, and is responsible for the hydraulic stress transmission between the vertebral body and the disc itself. The dome shaped middle of the end plate is mimicked by the secondary curvature in the disc implant of the present invention. The secondary arc which corresponds to the dome in the vertebral body provides a mechanism to lock the cage in place and prevent slippage or extrusion. The teeth 20 on the first and second faces 16, 18 of the implant 10 grip the vertebral body and cause a mechanical interface between the prosthesis 10 and the end plate of the vertebral body 42.

In another embodiment, depicted in FIG. 6, the implant 10 includes an insert of synthetic bone material 50, such as porous hydroxyapatite or other equivalent substance. Preferably, the synthetic bone material 50 is Interpore ProOsteon 500 brand of porous coralline hydroxyapatite, available from Interpore International, Irvine Calif. The porous synthetic bone material 50 is held in place by press fit (friction) and by the set screws 34 on the sides of the implant 10. The porous synthetic bone 50 allows independent placement of the implant 10 into the intervertebral disc space without use of a bone graft. This will prevent the morbidity and complications associated with harvesting a bone graft from the patient, reported to be as high as 21%. It will also obviate the need for use of an allograft, which carries the risk of disease transmission and added expense.

The implant 10 provides a non-articulating disc prosthesis which can be provided in multiple sizes depending on the size needed for the specific lumbar region, and can be furnished in smaller sizes for the cervical and thoracic spine as well as miniature cages for placement using endoscopic techniques for minimally invasive spine surgery.

The invention also provides a tool 60 (FIG. 9) for use in implanting an implant 10 in accordance with the present invention. The tool 60 includes a handle 62 and a pair of spaced arms 64, 66 extending perpendicularly therefrom. The arms 64, 66 are spaced to engage a pair of dimples 26 on an implant 10 or the oval slots 24. To use the tool, the surgeon merely inserts the arms 64, 66 into the notches 24 or dimples 26 until the implant 10 is held by the tool 60 and can be lifted. The implant 10 and the tool 60 can be furnished in kit form in a presterilized or sterilizable package (not shown).

During implantation surgery, the surgeon exposes the herniated or damaged disc, and removes it. A spinal disc implant 10 including a central core of porous synthetic bone, such as Interpore ProOsteon 500, is inserted using tool 60. The tool 60 grips the implant 10, which enables the surgeon to lift and insert the implant 10 in the intevertebral space defined by adjacent vertebral bodies from which the damaged or diseases disc was removed. The implant 10 is positioned on the vertebral body 42 (see FIG. 8) so that its transverse curvature conforms to the dome shape of the vertebral body 42. At the same time, the implant 10 is positioned so that its anterior to posterior position will create the proper angulation between vertebrae to help to restore the natural anatomic curvature of the human spine. The implant 10, once implanted, encourages osseointegration in two distinct ways. The teeth 20 found an irregular surface which grip the vertebral body and allow bone tissue to ground in and around the teeth 20. Also, the synthetic porous bone segment allows bone tissue to grow into the pores, to help anchor the implant 10 in place without resorting to bone grafts or allografts.

The following example is illustrative of the practices of the invention, and is not to be considered limiting.

EXAMPLE

A spinal disc implant 10 in accordance with the present invention implanted was implanted in the lumbar region spine of a patient. The implant additionally had porous synthetic bone (Interpore ProOsteon 500) in the central space, and pins were placed in the vertebrae above and below the implant 10 as an extra precaution to help insure that the implant 10 was securely held in place and that portion of spine did not articulate. To date this patient had no evidence of radiographic non-union and has had a satisfactory clinical outcome based upon range of motion, decreased pain, and return to prior activities.

Various modifications will be apparent to those skilled in the art. Such modifications and changes are intended to be included within the scope of the invention, which is defined by the following claims.

I claim:

1. A spinal disc implant comprising a ring-shaped body including a first pair of opposed substantially parallel sides spaced apart by a second pair of opposed sides to define a central bore, a first one of the second pair of sides defining a substantially arcuate curve joining a first end of the first pair of sides, a second one of the second pair of opposed sides joining a second end of the first pair of sides, upper and lower surfaces of the ring-shaped body having a plurality of teeth extending therefrom along a perimeter of the implant for engaging the adjacent vertebral bodies, the implant being made of a bicompatible metal; the first and second sides tapering from the second end to the first end and conforming to a curvature of a vertebral body on which the implant rests.

2. A spinal disc implant in accordance with claim 1 wherein the ring-shaped body is substantially oval.

3. A spinal disc implant in accordance with claim 1 wherein the ring-shaped body is substantially D-shaped.

4. A spinal disc implant in accordance with claim 3 wherein the biocompatible metal is titanium or alloys thereof.

5. A spinal disc implant in accordance with claim 3 wherein the central bore includes a porous hydroxyapatite block shaped to fill the central bore.

6. A spinal disc implant in accordance with claim 5 wherein the upper and lower surfaces of the ring-shaped body are convexly curved to mate with surfaces of adjacent endplates of vertebrae between which the implant is inserted.

7. A spinal disc implant in accordance with claim 5, wherein the implant includes a hole formed in the ring-shaped body, and further comprising a screw inserted in the hole for fixing the hydroxyapatite block in the central bore of the implant.

8. A spinal disc implant in accordance with claim 3 wherein the upper and lower surfaces of the ring-shaped body are curved to mate with adjacent endplates of vertebrae between which the implant is inserted.

9. A spinal disc implant having a generally elongated D-shaped body, the body tapering in thickness from a first end to a second end along first and second faces thereof, a degree of taper and thickness to allow the implant to fit within a cavity created by removal of a diseased or damaged vertebral disc and defined by an angle formed by adjacent vertebral bodies from between which the vertebral disc is removed, said spinal disc implant being of titanium or an alloy thereof and having a central bore open to first and second faces thereof being filled by a porous hydroxyapatite block shaped to substantially fill the central bore, the spinal disc implant additionally having a plurality of teeth projecting along the perimeter of the D-shaped body on the first and second faces for engaging bony and soft tissue of adjacent vertebrae, the teeth encircling the hydroxyapatite block and the second face convexly curved to mate with an overlying or underlying surface of a vertebral body on which the implant rests.

* * * * *